United States Patent [19]

Fujiwara et al.

[11] 4,173,943
[45] Nov. 13, 1979

[54] DEVICE FOR MOISTENING BLOOD SERUM BEARING FILM IN ELECTROPHORETIC APPARATUS

[75] Inventors: Toshihide Fujiwara, Fuchu; Nobutaka Kaneko; Ryo Fujimori, both of Hachioji, all of Japan

[73] Assignee: Olympus Optical Co., Ltd., Tokyo, Japan

[21] Appl. No.: 902,047

[22] Filed: May 2, 1978

[30] Foreign Application Priority Data

May 17, 1977 [JP] Japan .................. 52-56840

[51] Int. Cl.$^2$ ............... G01N 31/08; G01N 33/16
[52] U.S. Cl. ..................... 118/718; 118/68; 118/249; 118/72; 118/206; 427/2; 427/322; 427/428; 204/180 S; 204/299 R
[58] Field of Search .............. 204/180 S, 180 G, 299; 427/2, 322, 323, 324, 315, 428; 118/304, 206, 48, 249, 72, 68

[56] References Cited

U.S. PATENT DOCUMENTS

| 1,908,275 | 5/1933 | Youngchild et al. | 427/315 |
| 2,674,299 | 4/1954 | Bruker | 118/249 |
| 3,994,593 | 11/1976 | Kato et al. | 356/203 |
| 3,999,505 | 12/1976 | Kato et al. | 118/7 |
| 4,070,986 | 1/1978 | Kato et al. | 118/7 |

*Primary Examiner*—Ralph S. Kendall
*Attorney, Agent, or Firm*—Ostrolenk, Faber, Gerb & Soffen

[57] ABSTRACT

A device for moistening a blood serum bearing film before it is wetted with a buffer solution comprises a conveyor roller assembly including a first roller having its surface layer formed of sponge and partly maintained in immersion in a buffer solution and a second roller disposed above and in abutting relationship with the first roller, wetting means for passing a blood serum bearing film between the rollers to supply a buffer solution thereto from the surface layer, and a vapor ejection tube disposed adjacent to the both rollers for spraying a vapor to the film before it is wetted.

7 Claims, 7 Drawing Figures

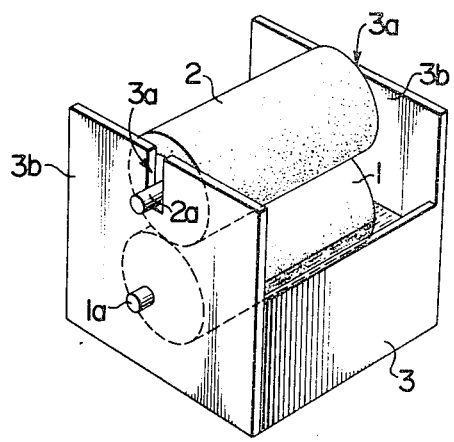
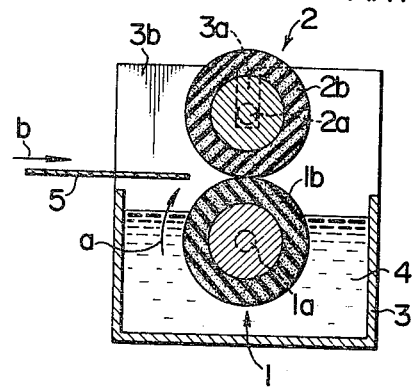
 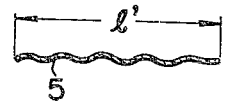
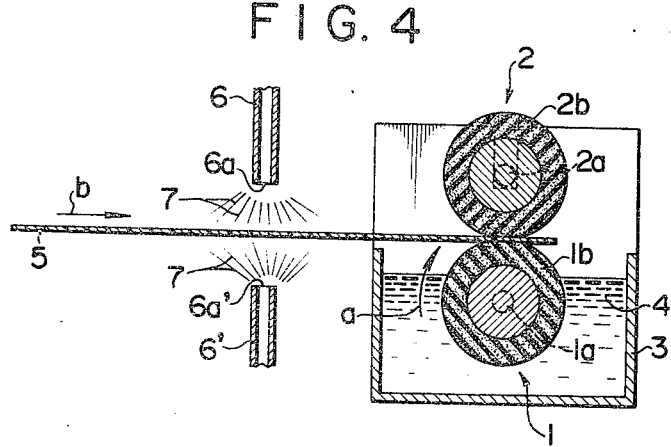

DEVICE FOR MOISTENING BLOOD SERUM BEARING FILM IN ELECTROPHORETIC APPARATUS

BACKGROUND OF THE INVENTION

The invention relates to a device for wetting a blood serum bearing film in electrophoretic apparatus, and more particularly, to such device which is adapted to be used in a blood serum analyzer of electrophoresis type.

As is well known, an electrophoretic apparatus achieves a fractionation of serum components applied to a bearing film by the process of electrophoresis. The fractionated components are determined with a densitometer or a photoelectric colorimeter of filter type for the purpose of quantitative analysis thereof. In such apparatus, the film is previously wetted with a buffer solution before a blood serum is applied thereto in order to facilitate the electrophoretic process to occur. Wetting device used at this end is already known. The film usually comprises a film of cellulose acetate while a buffer solution comprises Veronal-Veronal soda solution.

A conventional wetting device is shown in FIGS. 1 and 2, to which reference is made. The device includes a pair of upper and lower conveyor rollers 1, 2 having its surface layer 1b, 2b formed of a sponge material. A vessel 3 contains a quantity of buffer solution 4 such as Veronal-Veronal soda solution, and the pair of rollers are disposed therein so that the surface layer 1b of the lower roller 1 is maintained in immersion in the solution 4. The lower roller 1 has its drive shaft 1a rotatably mounted in the opposite sidewalls 3b of the vessel 3 at a level such that the surface layer 1b is partly immersed in the solution 4. The end of the drive shaft 1a, which is not visible in FIG. 1, extends out of the vessel to be connected with a suitable drive source to be driven for rotation in a direction indicated by an arrow a. The shaft 2a of the upper roller 2 has its opposite ends received in a pair of notches 3a formed in the top end of the both sidewalls 3b of the vessel 3 so as to be rotatable and also movable in the vertical direction. The arrangement is such that the upper roller is maintained in abutment against the lower roller by gravity.

In operation, when a blood serum bearing film 5 such as that formed by cellulose acetate is fed in a direction indicated by an arrow b (see FIG. 2) to be passed between the rollers 1, 2 by rotating the latter in the direction of the arrow a, the buffer solution 4 contained in the surface layer 1b of the lower roller wets the film, thus automatically achieving a wetting of the film.

However, such conventional arrangement suffers from the disadvantage that creases or crimples are formed in the film surface along the feed direction thereof while it passes between the rollers to be wetted with the buffer solution 4. Specifically, when wetted with the buffer solution, the film 5 immediately tends to expand in both feed and width directions. However, because the film 5 is held between the both rollers 1, 2, it cannot expand in the width direction. As a consequence, the width 1' of the film 5 after the wetting process (see FIG. 3B) remains substantially equal to the width 1 before the wetting process shown in FIG. 3A, but creases are formed in the feed direction in order to accommodate for the elongation in the width direction. The rate of expansion of the cellulose acetate film varies with the film composition, lot and manufacturers, but ranges from zero to several percent, resulting in a relatively large variation from film to film. It is known that the formation of creases will be greater with a film having a greater rate of expansion. The blood serum cannot be uniformly applied to a film having such creases formed therein. In addition, the presence of creases interferes with the electrophoretic process of the serum components, preventing a smooth formation of a fractionated pattern from being formed.

SUMMARY OF THE INVENTION

It is an object of the invention to provide a wetting device for a blood serum bearing film used in an electrophoretic apparatus which avoids such disadvantage of the prior art.

In accordance with the invention, the blood serum bearing film is moistened with a vapor before it is wetted with the buffer solution. As a consequence, an expansion has already taken place in the film when it is subjected to the wetting step, thus preventing the occurrence of creases.

BRIEF DESCRIPTION OF THE DRAWINGS

FIG. 1 is a perspective view of a conventional wetting device;

FIG. 2 is a longitudinal section of the device shown in FIG. 1;

FIGS. 3A and B are cross sections of a film illustrating the film before and after the wetting process;

FIG. 4 is a longitudinal section of a wetting device according to one embodiment of the present invention;

DESCRIPTION OF PREFERRED EMBODIMENTS

Figure 5:
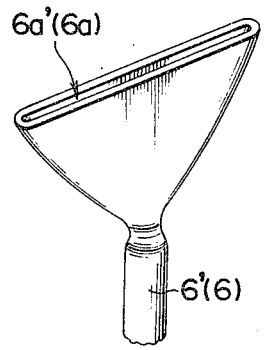
FIG. 5 is a perspective view of a vapor ejection port.

Referring to FIG. 4, there is shown a wetting device according to one embodiment of the invention. The general arrangement of the wetting device is similar to the prior art arrangement shown in FIGS. 1 and 2, and therefore similar parts are designated by like reference characters and will not be described in detail. Instead, the following description is directed primarily to the difference between the arrangement of the invention and the prior art.

In FIG. 4, a pair of vapor ejection tubes 6, 6' are disposed above and below a path for conveyance of the film 5 at a position forwardly of the rollers 1, 2 or to the left thereof. These tubes have exhaust nozzles 6a, 6a' which are located opposite to each other. As shown in FIG. 5, the nozzle 6a' has an opening which is elongate along the width direction of the film 5. The tubes 6, 6' are connected with a vapor generator, not shown, for injection of vapor 7 from the respective nozzles 6a, 6a'.

The vapor 7 may comprise a steam or a vapor which is formed by the vaporization of the buffer solution 4. It is preferred to utilize an ultrasonic heater for the vapor generator, which produces a mist of small particle sizes without utilizing the heating means. However, it should be understood that an atomizer which utilizes the heating or mechanical means may also be used.

In the use of the wetting device of the invention, the roller 1 is driven for rotation in the direction of the arrow a as shown in FIG. 4, and the tubes 6, 6' are activated for injection of the vapor 7 from their nozzles.

The film 5 can then be fed in the direction of the arrow b as shown in FIG. 4 to be passed between the rollers 1, 2. Thereupon, as a result of the film 5 being sprayed with vapor 7, a free expansion occurs in both feed and width directions before it is passed between the rollers. The absence of any restriction upon the expansion of the film avoids any limitation on the expansion of the film 5 in any direction. Since the film has fully expanded before it is passed between the rollers, no further expansion and hence no crease is produced when it is wetted with the buffer solution 4 during its passage between the rollers. The amount of vapor 7 which is sprayed to the film 5 is substantially smaller than the amount of buffer solution 4 which is used to wet the film, so that there is no significant adverse influence upon forming an electrophoretic pattern.

The pair of vapor ejection tubes 6, 6' may be replaced by a plurality of narrower tubes which are spaced apart along the width direction of the film 5. Alternatively, a single one of the tubes 6, 6' may be used. In the embodiment shown, the both rollers 1, 2 have their surface layers 1b, 2b formed of a sponge material, but it is also possible to use a sponge surface layer for the lower roller 1 alone without causing any impediment upon the wetting process.

Figure 6:
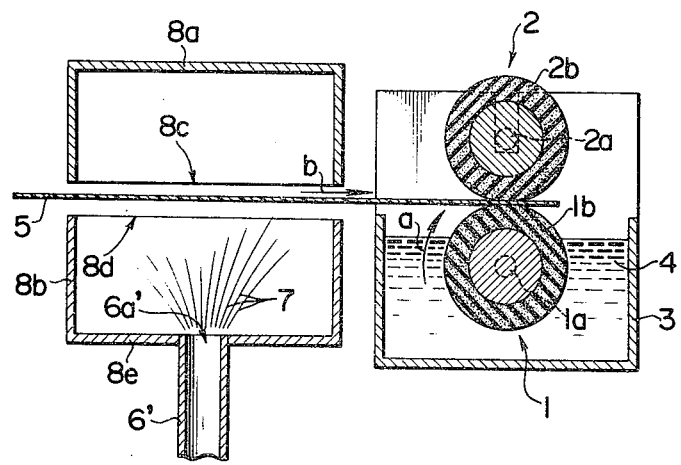
FIG. 6 is a longitudinal section of another embodiment of the present invention.
Figure 7:
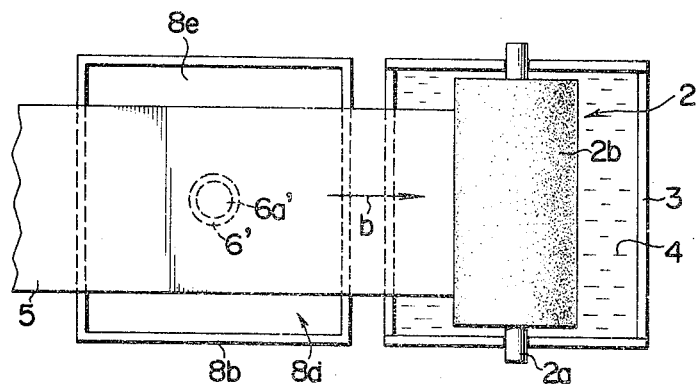
FIG. 7 is a plan view of the wetting device shown in FIG. 6 with the upper vapor casing half removed.

FIG. 6 shows another embodiment of the invention which utilizes a single vapor ejection tube 6'. Since it is necessary to spray vapor 7 over an expanded area so that the film 5 may be uniformly moistened, it involves an extended scattering of vapor 7 beyond the region of the film 5. To prevent this, a pair of upper and lower casings 8a, 8b are disposed above and below the path of conveyance of the film at position forwardly of the conveyor rollers 1, 2 or to the left thereof, as viewed in FIGS. 6 and 7. The casings 8a, 8b form an enclosure for confining the vapor, thus preventing an extended scattering of vapor 7 beyond the region of the film 5. The upper casing 8a has a bottom opening 8c which faces the path while the lower casing 8b has a top opening 8d which faces the path or the bottom opening 8c of the upper casing 8a. The width of the both openings 8c, 8d is slightly greater than the width of the film 5 so as to permit a complete coverage of the film. A vapor ejection tube 6' has its exhaust nozzle 6a' opening substantially in the center of the bottom wall 8e of the lower casing 8b.

In operation, vapor 7 which is dumped from the nozzle 6a' toward the film 5 uniformly moistenes the film while the lower casing 8b prevents a scattering of the vapor to regions other than the film. The vapor which rises from adjacent the lateral edges of the film 5 will be recovered by the upper casing 8a, thus again preventing a scattering of the vapor to the surrounding atmosphere. When there is no film 5 which passes through the space between the both openings 8c, 8d, vapor 7 dumped by the nozzle 6a' will be completely recovered by the both casings 8a, 8b, thus completely preventing a scattering of the vapor to the outside.

It should be noted that the vapor ejection tube 6' may be mounted in the upper casing 8a as well. Alternatively, such tube may be mounted on both casings, and the tubes can be mounted on these casings in any suitable manner.

What is claimed is:

1. A device for wetting a blood serum bearing film in electrophoretic apparatus, comprising a first roller having a surface layer formed of a sponge material and disposed so that the surface layer is partly maintained in immersion in a buffering solution, a second roller disposed above and in abutting relationship with the first roller, wetting means for passing a blood serum bearing film between the rollers to wet the film with the buffer solution that is contained in the surface layer while the film passes between the rollers, and a vapor ejection tube disposed forwardly of the rollers for moistening the film by the application of a vapor thereto before the film is wetted.

2. A device according to claim 1 in which the vapor ejection tube has an exhaust nozzle which is elongate along the width direction of the film.

3. A device according to claim 1 in which a pair of vapor ejection tubes are disposed above and below a path of conveying the film in a manner such that their exhaust nozzles face each other.

4. A device according to claim 1 in which the vapor ejection tube comprises a plurality of narrower tubes spaced apart along the width direction of the film.

5. A device according to claim 1 in which the vapor applied to the film comprises a steam or a vapor which is formed by the evaporation of the buffer solution.

6. A device according to claim 1, further including a vapor enclosure which prevents a scattering of the vapor to regions other than the film.

7. A device according to claim 6 in which the vapor enclosure comprises an upper and a lower vapor casing, which are disposed above and below a path of conveyance of the film with their openings facing each other, the exhaust nozzle of the vapor ejection tube opening into at least one of the casings.

* * * * *